United States Patent
Cole et al.

[19]

[11] Patent Number: 5,968,027
[45] Date of Patent: Oct. 19, 1999

[54] ABSORBENT ARTICLE WITH COILED SIDE WALLS

[75] Inventors: Robert Cole, Jackson; Raymond J. Hull, Jr., Hampton, both of N.J.

[73] Assignee: McNeil-PPC, Inc., Skillman, N.J.

[21] Appl. No.: 08/829,013

[22] Filed: Mar. 31, 1997

[51] Int. Cl.$^6$ ................................................. A61F 13/15
[52] U.S. Cl. ..................... 604/385.1; 604/378; 604/358
[58] Field of Search ................................ 604/358, 378, 604/385.1, 386, 387

[56] References Cited

U.S. PATENT DOCUMENTS

| | | | |
|---|---|---|---|
| 2,507,197 | 5/1950 | Metzdort | 604/377 |
| 3,612,055 | 10/1971 | Mesek | 604/378 |
| 3,699,966 | 10/1972 | Chapuis | 604/378 |
| 3,731,688 | 5/1973 | Litt | 604/378 |
| 3,968,798 | 7/1976 | Hokanson | 604/378 |
| 4,029,101 | 6/1977 | Chesky et al. | 604/378 |
| 4,505,705 | 3/1985 | Matthews et al. | 604/385.1 |
| 4,731,070 | 3/1988 | Koci | 604/385.1 |
| 4,781,711 | 11/1988 | Houghton et al. | 604/378 |
| 4,787,896 | 11/1988 | Houghton et al. | 604/385.1 |
| 4,795,453 | 1/1989 | Wolfe | 604/385.1 |
| 5,300,054 | 4/1994 | Feist et al. | 604/378 |
| 5,575,781 | 11/1996 | DeBusk | 604/362 |
| 5,713,885 | 2/1998 | Jorgenson et al. | 604/385.1 |

FOREIGN PATENT DOCUMENTS

| | | |
|---|---|---|
| 0441064 A1 | 8/1991 | European Pat. Off. . |
| 0543116 A1 | 5/1993 | European Pat. Off. . |
| WO 91/09582 | 7/1991 | WIPO . |
| WO 93/06804 A1 | 4/1993 | WIPO . |
| WO 96/20678 A1 | 7/1996 | WIPO . |

*Primary Examiner*—Mark O. Polutta
*Attorney, Agent, or Firm*—Joel A. Rothfus

[57] ABSTRACT

The absorbent structure of the invention has a substantially continuous absorbent web having an absorbent layer and a transfer layer. The transfer layer includes a nonabsorbent material and is capable of transferring liquids which it receives to the absorbent layer. The first and second edges of the absorbent web are coiled to form side walls, and the side walls form a trough therebetween. The top, trough-containing surface provides a natural trough in the space between the side walls for receiving and holding large gushes of body fluid until they can be absorbed by or dispersed into the rest of the structure.

20 Claims, 5 Drawing Sheets

ABSORBENT ARTICLE WITH COILED SIDE WALLS

BACKGROUND OF THE INVENTION

The present invention relates to a new and improved absorbent structure which may be used in a disposable absorbent article having a fast liquid penetration rate and high liquid retention, and which allows the skin of a wearer to remain dry even after the article has become wet.

Disposable absorbent articles have long been used to absorb body exudates to prevent staining or soiling of a wearer's clothing. Examples of such articles include feminine sanitary napkins, diapers, and adult incontinence products. Initially, such articles had absorbent cores constructed primarily of traditional cellulosic fiber materials, such as tissue wadding and/or wood pulp fluff. These cellulosic fiber materials demonstrate good dry resilience and good absorbency for body fluids. However, once cellulosic fiber materials become wet, they tend to "collapse" and lose their resilience. In other words, the wet cellulosic fibers become limp and compacted together, thereby causing the structure to lose the fluid-holding benefit of the spaces between the fibers. Furthermore, such wet cellulosic fiber materials are unable to absorb further additions of fluid, otherwise known as repeat fluid insults. Wet cellulosic fiber products also provide an unpleasant wet, soggy feeling against a wearer's skin.

More recently, superabsorbent particles have been added to cellulosic fiber materials in disposable absorbent articles to improve their absorbent capacity and to provide the articles with a drier feel against a wearer's skin. Although superabsorbent particles do not collapse when wet, they do not absorb fluid as rapidly as cellulosic fiber materials. Large volumes of fluid added rapidly to a superabsorbent material will tend to run off if not held in fluid contact with the superabsorbent for some time. Therefore, it has also become common to use so-called transfer layers between the absorbent core and the body-facing surface of the article. Transfer layers are generally resilient fibrous webs which provide void volume for rapidly taking up fluid and then releasing it more slowly to the adjacent absorbent core to allow time for the superabsorbent materials to absorb the fluid. Transfer layers also provide an insulating layer between the absorbent core and the wearer, preventing contact between a wet absorbent core and the wearer's skin. Such transfer layers are somewhat limited, however, since their fluid-transporting effectiveness depends upon their intimate contact with the underlying absorbent core. Therefore, the article must be constructed such that the transfer layer remains in good contact with the absorbent core during wearing conditions. The inherent void volume of the transfer layer, and thus its liquid-holding capacity, is limited by its thickness; i.e., a thicker transfer layer provides greater void volume, but if it is too thick, it becomes bulky and therefore, uncomfortable and indiscreet to the wearer. Therefore, thin transfer layers are preferred for wearer comfort, but their small void volume allows them to hold only a small volume of fluid.

The object of this invention is to provide an absorbent structure with a fast fluid penetration rate for initial fluid add-on and for repeat fluid insults, good wet and dry resilience, and good surface dryness.

SUMMARY OF THE INVENTION

The absorbent structure of the invention has a substantially continuous absorbent web having first and second opposed side edges which are arranged substantially parallel to the structure's longitudinal axis. The absorbent web has an absorbent layer and a transfer layer. The transfer layer includes a nonabsorbent material and is capable of transferring liquids which it receives to the absorbent layer. The absorbent layer defines an absorbent layer surface and the transfer layer defines a transfer layer surface on the opposite side of the web. The first edge of the absorbent web is manipulated to bring a region of the transfer layer surface proximate the first edge into contact with a region of the absorbent layer surface to form a first enhanced portion, and the second edge of the absorbent web is manipulated to bring a region of the transfer layer surface proximate the second edge into contact with a region of the absorbent layer surface to form a second enhanced portion. Preferably, the enhanced portions are coiled portions of the absorbent web which form side walls. The resulting absorbent structure has two coiled side walls on its top surface and is substantially flat on its bottom surface. The top surface provides a natural trough in the space between the side walls for receiving and holding large gushes of body fluid until they can be absorbed by or dispersed into the rest of the structure.

The term "substantially coiled" as used herein may be defined as being wound or folded into a roll. Such a substantially coiled structure may thus have a rounded, an oval, or a flattened profile. Relatively stiff or thick materials provide a rounded structure when substantially coiled; however, thinner and softer materials provide a more oval or even flat structure when substantially coiled. Very thin or soft materials may need to be folded to obtain the substantially coiled structure of the invention.

The term "substantially completely enclosed" is used herein to indicate that the substantially coiled side walls must be wound at least 360 degrees or folded over at least two times so that the side edges of both the absorbent and transfer layers are completely contained within the interior of the side walls.

DETAILED DESCRIPTION OF THE PREFERRED EMBODIMENT

Figure 1:
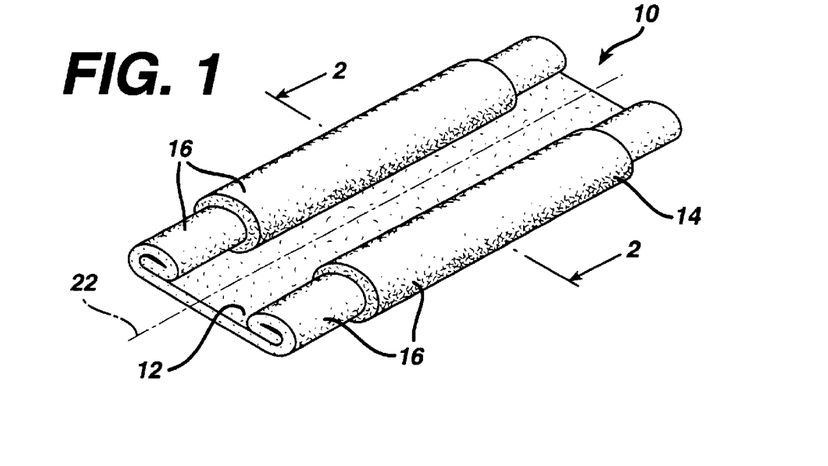
FIG. 1 is a perspective view of one embodiment of the present invention.
Figure 2:
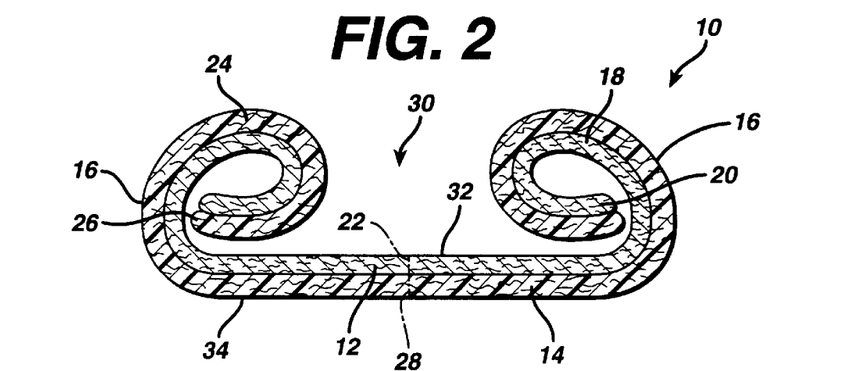
FIG. 2 is a cross-sectional view taken along line 2—2 of the embodiment illustrated in FIG. 1.

In its simplest embodiment, shown in FIGS. 1 and 2, the absorbent structure 10 of the invention has a substantially continuous absorbent web. The absorbent web has an absorbent layer 12 and a resilient or transfer layer 14, and it is configured to form enhanced portions or side walls 16. The absorbent layer 12 has sides 18 terminating in edges 20 and a longitudinal center line 22 parallel to the sides 18 and edges 20. The transfer layer 14 also has sides 24 terminating in edges 26, and a center line 28 parallel to the sides 24 and edges 26. The absorbent layer 12 is layered over the transfer layer 14 such that the center line 22 of the absorbent layer overlies the center line 28 of the transfer layer. The sides 18, 24 of the overlying layers are then collectively rolled or folded toward the absorbent layer center line 22 to form substantially coiled side walls 16. Preferably, the edges 20, 26 of the absorbent and transfer layers contained within the side walls 16.

The side walls 16 may be rolled or folded any number of times, preferably to provide at least about three layers of the web in the enhanced portion. In addition, it is preferred that the edges 20, 26 of the absorbent layer 12 and transfer layer 14 are completely contained within the side walls 16. A portion of the absorbent layer 12 may be visible between the side walls 16 (see FIG. 3) or the side walls 16 may abut one another along the center line 22 of the absorbent layer 12. In any case, the side walls 16 define a natural trough 30 between them.

The absorbent layer of the structure may comprise any known absorbent materials including but not limited to absorbent fibers such as wood pulp fluff, rayon fibers, cotton fibers, and the like; superabsorbent fibers or particles; other naturally occurring absorbent materials such as peat moss; and other synthetic absorbent materials such as foams and the like. The absorbent layer may also include one or more of the following: thermoplastic binder fibers, latex binder, perfumes, or odor-controlling compounds. The absorbent layer may be compressed or uncompressed, embossed, or calendered. In a preferred embodiment, the absorbent layer consists of a blend of wood pulp, synthetic wood pulp, and superabsorbent polymer particles airlaid onto a single ply of tissue. This blend is available as RC#000004 a roll good from Merfin Hygienics Company in Canada. In this embodiment of the invention, the Merfin absorbent blend is unrolled and embossed to form embossing channels.

The transfer layer may comprise any known material which will take up fluid and then distribute and release it to an adjacent absorbent layer for storage. Preferred transfer layers have a relatively open structure which allows for free movement of fluid within the layer. Suitable materials for such transfer layers include fibrous webs, resilient foams, and the like.

The transfer layer, existing as a mass of these materials, is able to accept fluid and allow passage of the fluid through its mass to be absorbed by an adjacent absorbent core. Therefore, the mass of materials may be absorbent, although the materials themselves are not absorbent. Thus, transfer layers which are made of hydrophobic, nonabsorbent fibers may be able to accept large volumes of fluid into the interfiber void spaces while the fibers themselves do not absorb any significant quantities of fluid. Likewise, open-celled foam structures which are made from nonabsorbent materials may also absorb fluid into the cells of the foam. The walls of the cells, however, do not absorb any fluid. The cumulative spaces within the transfer layer, i.e., the interfiber void spaces in the fibrous transfer layer or the open cells in the foam transfer layer, function much like a container to hold fluid.

Preferred transfer layer fibrous webs are made of resilient, nonabsorbent materials to provide void volume and to allow for free movement of fluid through the structure. Transfer layers that are made from webs of mostly absorbent fibers absorb the fluid as it enters the structure and do not distribute it throughout the rest of the structure as efficiently as webs containing non-absorbent materials. In a particularly preferred embodiment of the present invention, the transfer layer comprises a carded and through-air bonded web of a blend of 40% by weight of high denier polyester fibers (15 denier fibers available as Polyester 374 from Celanese), and 60% by weight of bicomponent binder fibers having a polyester core and a polyethylene sheath (10 denier fibers available as 1036 bicomponent fibers from BASF).

Figure 3:
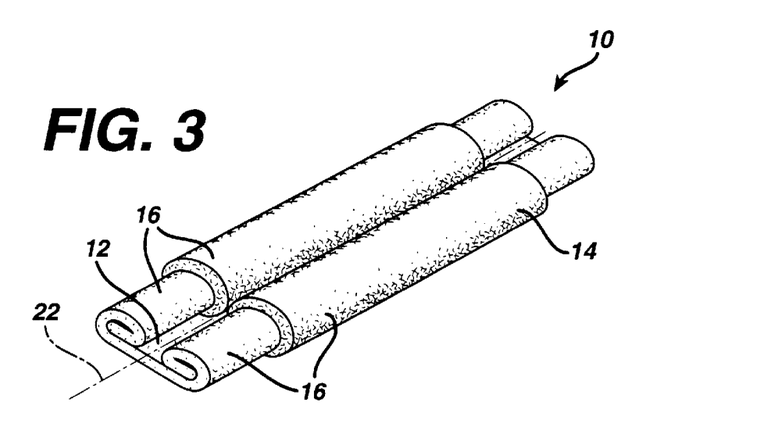
FIG. 3 is a perspective view of another embodiment of the present invention.

The article is assembled by placing the absorbent layer 12 over the transfer layer 14 such that the center line 22 of the absorbent layer overlies the center line 28 of the transfer layer. This forms the absorbent web which has an absorbent layer surface 32 and a transfer layer surface 34. The absorbent layer surface 32 is generally formed by the upper surface of the absorbent layer, although additional elements which do not detrimentally affect the fluid handling properties of the absorbent structure can be applied to the absorbent layer to form the absorbent layer surface 32. In addition, the transfer layer surface 34 is generally formed by the lower surface of the transfer layer, although additional elements which do not destroy the fluid handling properties of the absorbent structure can be applied to the transfer layer to form the transfer layer surface 34. For example, a nonwoven or apertured film covering veneer could be applied to either the top of the absorbent layer 12 or the bottom of the transfer layer 14. The side portions of the two layers are then collectively rolled or folded toward the absorbent layer center line at least until the side edges 20, 26 of both the absorbent layer and the transfer layer are completely contained within the rolls or folds 16. These rolls or folds 16, otherwise known as side walls in the present invention, may abut one another over the absorbent layer center line 22, as shown in FIG. 1. Alternatively, they may be set back somewhat from either side of the absorbent layer center line 22, leaving a strip of absorbent layer 12 visible between the side walls 16, as shown in FIG. 3. In either case, the side walls define a natural trough therebetween.

Figure 4:
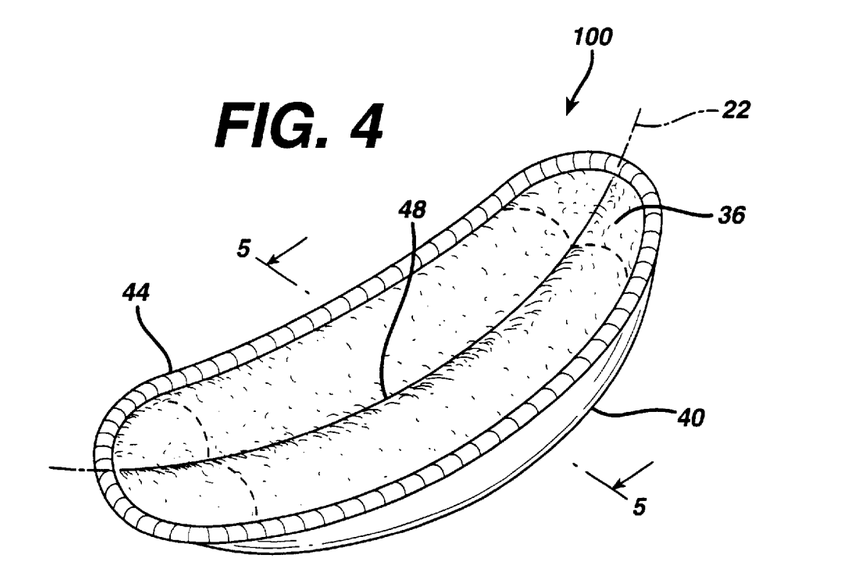
FIG. 4 is a perspective view of a further embodiment of the present invention.
Figure 5:
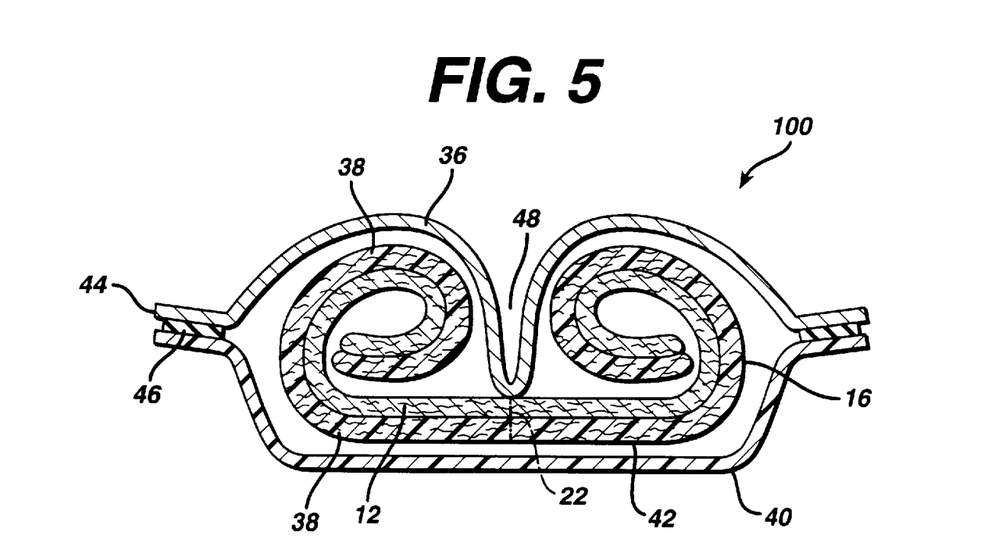
FIG. 5 is across-sectional view taken along line 5—5 of the embodiment illustrated in FIG. 4.

A preferred embodiment of an absorbent article 100 with the absorbent structure 10 of the present invention is shown in FIGS. 4 and 5. A body-facing cover layer 36 is placed over the trough-containing surface 38 of the absorbent structure, that is, the surface on which the trough is located. Preferably, the body-facing cover 32 is attached to the absorbent layer center line 22 between the side walls 16. A fluid-impermeable barrier 40 is placed under the lower surface 42, opposite the trough-containing surface 38. It is preferred that the body-facing cover 32 and the fluid-impermeable barrier 40 are attached to one another around the periphery of the article by means of flange seals 44. Elastic means 46 may be provided along or within at least a portion of the flange seals 44 to cause the article to assume a curved, boat-shape as shown in FIG. 4. Useful elastic means are known and can be elastic foams, elastic strips or bands, elastic threads, and the like. Such articles made from the absorbent structure of the present invention have a longitudinal center line 48 corresponding to the center lines 22, 28 of the absorbent layer 12 and the transfer layer 14.

Figure 6:
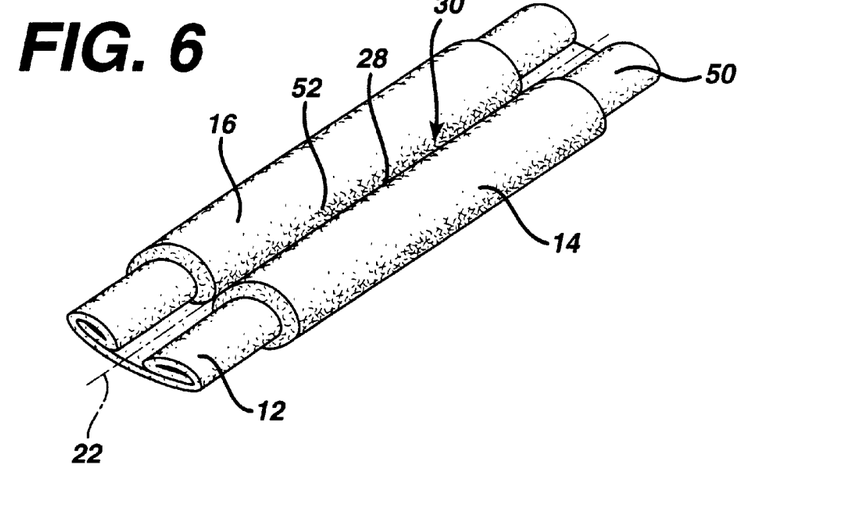
FIG. 6 is a perspective view of another embodiment of the present invention.

In a most preferred embodiment, shown in FIG. 6, the dimension of the absorbent layer 12 as measured along its center line 22, is greater than the dimension of the transfer layer 14 as measured along the transfer layer center line 28. The transfer layer 14 is centered with respect to the absorbent layer 12, thereby allowing absorbent layer extensions 50 to project beyond the transfer layer 14. These extensions 50 become the ends of the side walls 16. Preferably, at least one of the extensions 50 is densified, e.g., by calendering, embossing, compression, or the like, so that an absorbent article formed from the structure has at least one tapered end for greater discretion and wearing comfort. Most preferably, both of the extensions 50 are calendered for maximum discretion and wearing comfort. The extensions 50 may further serve as indicators to the wearer that the article is saturated and needs to be changed by providing a wet feel to the wearer's skin when the extensions become saturated.

In this preferred embodiment, fluid enters the article in the central transfer layer-containing portion 52, where it is quickly captured and distributed to the absorbent core 12. The article is especially effective at capturing gushes of fluid in the trough 30 formed by the side walls 16. The captured fluid is quickly distributed into the absorbent core 12 by the transfer layer 14 and the side walls 16. Subsequent gushes are then quickly captured and distributed, as well. Since the transfer layer 14 does not contain absorbent material, it does not retain fluid, and therefore presents a dry feel on both the trough-containing surface 38 and the lower surface 42. The absorbed fluid is transferred to the absorbent core 12, which becomes saturated first in the center and then at the ends. However, the side wall configuration provides good fluid transport throughout the structure, so that, even when the central portion of the absorbent core is saturated, subsequent gushes of fluid are taken up quickly and are transported out toward the ends of the structure. When most of the absorbed fluid is contained within the central transfer layer-containing portion 52 of the structure, the exposed surfaces of the structure remain dry to the touch. As the exposed extensions 50 of the absorbent core 12 become saturated, the wearer feels the wetness as a signal that it is time to change the article.

Figure 7:
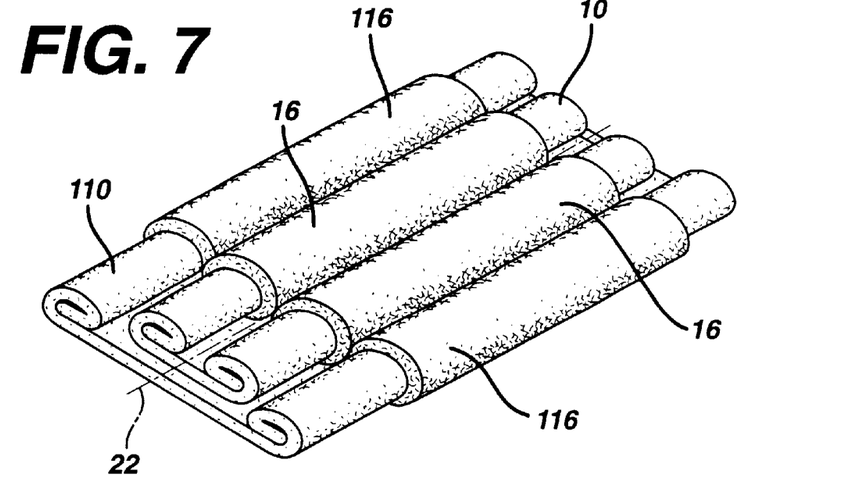
FIG. 7 is a perspective view of a further embodiment of the present invention.

In a further embodiment, as shown in FIG. 7, a second absorbent layer/transfer layer structure 110 is layered under a first such structure 10 such that the first structure 10 is contained within the trough of the second structure 110. Side walls 116 formed by the sides of the second structure 110 abut the side walls 16 of the first structure 10.

Figure 8:
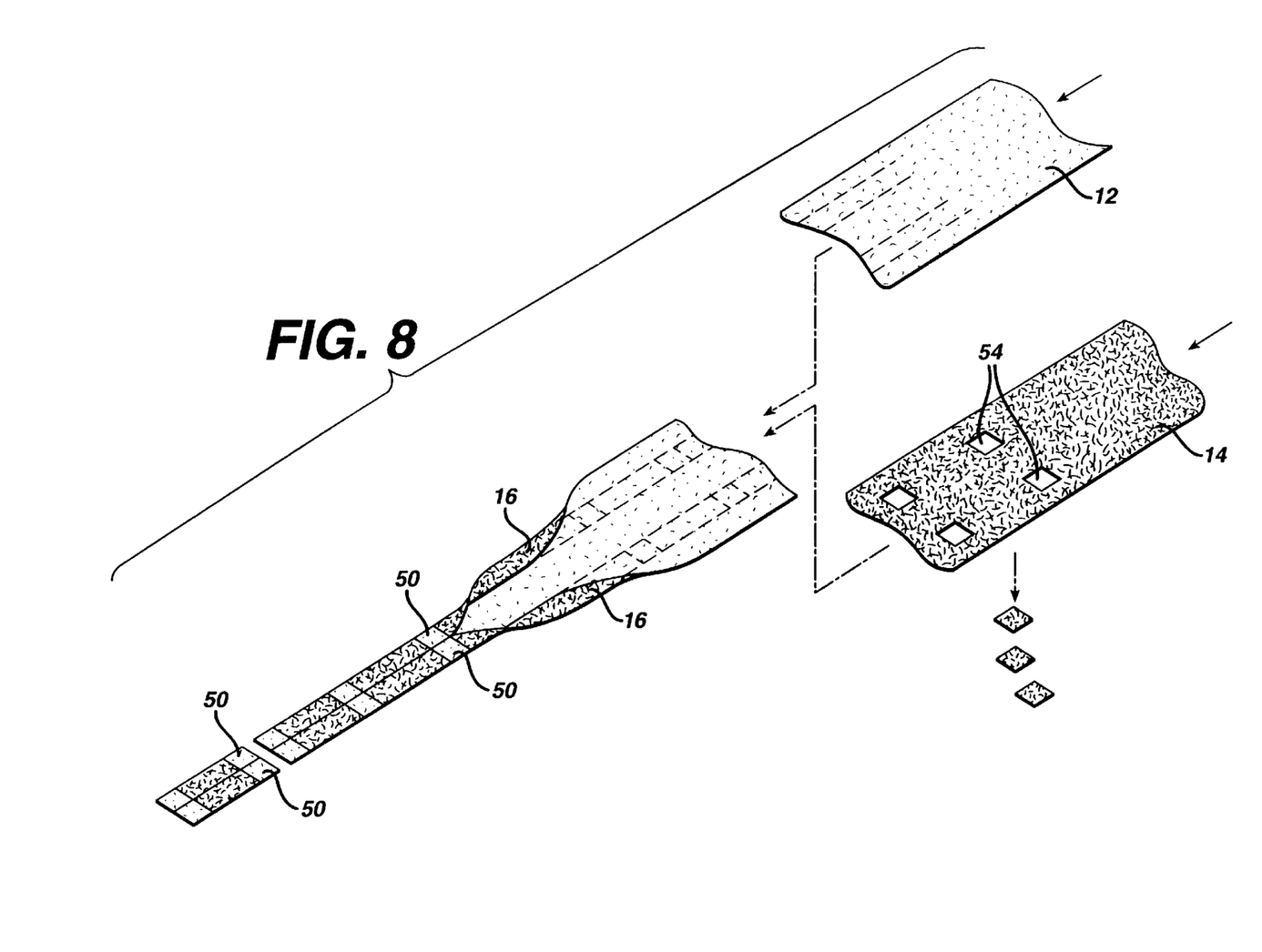
FIG. 8 is a simplified illustration of a method of making an absorbent structure according to the present invention.
Figure 9:
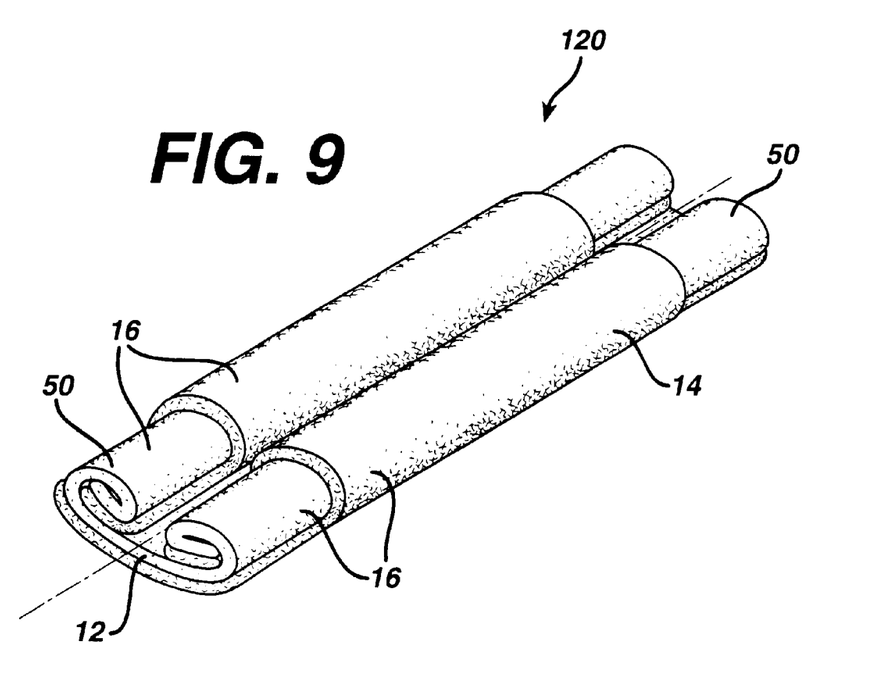
FIG. 9 is a perspective view of an embodiment of the present invention made by the method illustrated in FIG. 8.

A simple method of making the article of the invention with exposed extensions is illustrated in FIG. 8. FIG. 8 shows the absorbent layer 12 and transfer layer 14 being brought together before the coiled side walls 16 are formed. The method of FIG. 8 allows for continuous assembly of absorbent structures with exposed extensions 50 without the need to cut shorter transfer layers 14 and place them over longer absorbent layers 12. The method of FIG. 8 shows windows 54 being cut from the transfer layer 14 at predetermined locations. The locations correspond to the trough-containing surface of the ends of the side walls. The windows 54 provide exposed extensions 50 without the need to cut and place segments of absorbent layers and transfer layers. The exposed extensions 50 illustrated in FIG. 8 offer the advantages of tapered ends and wetness indication. An absorbent structure made by the method of FIG. 8 is illustrated in FIG. 9.

EXAMPLE 1

A product according to the present invention was prepared as follows. A transfer layer sheet of 7-inch×9-inch carded, through-air bonded web comprising a blend of 60% BASF #1036 bicomponent binder fiber (10 denier) and 40% Celanese polyester #374 fiber (15 denier) was provided. A 9-inch square absorbent layer sheet containing a blend of 7 grams of Arakawa 751 superabsorbent and 10.5 grams of pulp on a tissue carrier was placed over and centered on the transfer layer sheet. Two opposed edges of the absorbent layer sheet aligned with two opposed edges of the transfer layer sheet. The other two edges of the absorbent layer sheet extended one inch beyond the other two edges of the transfer layer sheet. The aligned edges of the transfer layer sheet and the overlying absorbent layer sheet were then collectively rolled over the absorbent layer sheet toward the center line of the absorbent layer sheet to form first and second side walls with a trough between them. The ends of the structure were then calendered to provide densified and tapered ends and to help maintain the configuration of the side walls during the product construction process.

One surface of a nonwoven sheet (4109 Enka from Fibertech) was coated with adhesive, and the sheet was placed adhesive-side down over the side walls and the trough, that is, the trough-containing surface of the structure. The sheet was pressed down and adhered to the absorbent core surface in the trough between the two side walls. A barrier film was placed over the opposite surface of the structure. Elastic foam strips were attached to the barrier film along two edges such that the foam strips were parallel to the side walls when the article was assembled. The barrier and the nonwoven cover were joined to one another around the peripheral edges of the structure to form flanges with the elastic foam strips enclosed within the flanges. The elastic foam strips caused the article to assume a curved, boat-shape for good fit to the body, and the tapered ends provided wearing discretion and comfort.

Surface Wetness Test

The Surface Wetness Test measures the amount of fluid that is squeezed out through the body-facing surface of a wet absorbent article under a pressure of about 0.5 psi. The test is performed by placing an article on a flat surface with its body-facing surface oriented upward. A separatory funnel is suspended over the article with the lower tip of the funnel positioned at a distance of 1 inch from the surface of the article. The funnel is used to dispense 200 ml of test fluid at a rate of 20 ml/minute onto the top surface of the article. The test fluid comprises 1.59% saline with a surface tension of 62.26 dyne. The fluid that runs over the sides of the article is captured and weighed to determine the Pad Overflow. After 15 seconds, a preweighed filter pad is placed over the body-facing surface of the article, and a pressure of 0.5 psi is applied to the top of the filter pad for 2 minutes. The wet filter pad is then weighed. The difference between the wet filter pad weight and the dry filter pad weight determines the amount of fluid absorbed. If the amount absorbed is less than 1 gram, the test is complete. If the amount is greater than 1 gram, another dry preweighed filter pad is placed over the body-facing surface of the article, and the 0.5 psi pressure is applied to the filter pad for 2 minutes. The wet filter pad is then removed and weighed to determine the amount of fluid absorbed. If the amount of fluid absorbed is less than 1 gram, the test is complete. If the amount of fluid absorbed is greater than 1 gram, the test is continued in the same manner until the wet filter pad has absorbed less than 1 gram of fluid. When the test is complete, the total amount of fluid absorbed from all of the filter pads is added to the amount of the Pad Overflow and this sum is reported as the Surface Wetness.

TABLE I

| | Surface Wetness | | | | | |
| --- | --- | --- | --- | --- | --- | --- |
| | Example 1 | | POISE ™ Super Absorbency Plus Guard | | POISE ™ Extra Absorbency Plus Pad | |
| | Surf. Wet. (gr.) | Std. Dev. | Surf. Wet. (gr.) | Std. Dev. | Surf. Wet. (gr.) | Std. Dev. |
| | 10.31 | 1.00 | 86.33 | 6.13 | 64.19 | 6.40 |

Table I shows the Surface Wetness data for 5 samples each of the article of Example I, POISE Superabsorbency Plus Guards, and POISE Extra Absorbency Plus Pads. POISE is a trademark of Kimberly-Clark Corporation. Both of the POISE articles demonstrated fluid overflow during the test, but neither Example had fluid overflow. Furthermore, the POISE articles had Surface Wetness values much higher than those of Example 1. It is desired that absorbent articles demonstrate low surface wetness for wearer comfort. Any fluid remaining on the body-facing surface of the article is free to either run off the article to stain the wearer's clothing, or to wet the wearer's skin. Skin that is in prolonged contact with body fluid is susceptible to irritation and infection. Furthermore, the wetness of the article against the wearer's skin is uncomfortable to the wearer. The article of Example 1, with a nonabsorbent transfer layer, had reduced surface wetness over a similar article with an absorbent transfer layer and over similarly sized commercially available products.

The specification and embodiments are presented to aid in the complete and non-limiting understanding of the invention disclosed herein. Since many variations and embodiments of the invention can be made with out departing from its spirit and scope, the invention resides in the claims hereinafter appended.

What is claimed is:

1. An absorbent structure having a longitudinal axis and comprising a substantially continuous absorbent web having first and second opposed side edges arranged substantially parallel to the longitudinal axis of the structure, the absorbent web comprising an absorbent layer in liquid communication with a transfer layer capable of transferring liquid to the absorbent layer, the transfer layer comprising a nonabsorbent material wherein:
   (1) the absorbent layer is superposed over the transfer layer to provide an outwardly facing absorbent layer surface and an opposed outwardly facing transfer layer surface;
   (2) the first edge of the absorbent web is arranged and configured wherein a region of the outwardly facing transfer layer surface proximate the first edge contacts a region of the outwardly facing absorbent layer surface to form a first enhanced portion; and
   (3) the second edge of the absorbent web is arranged and configured wherein a region of the outwardly facing transfer layer surface proximate the second edge contacts a region of the outwardly facing absorbent layer surface to form a second enhanced portion.

2. The absorbent structure of claim 1 in which the transfer layer has at least one window provided therein at a predetermined location, thereby exposing the absorbent layer at the location.

3. The absorbent structure of claim 2 in which the structure has first and second ends substantially perpendicular to the longitudinal axis, the at least one window being located in at least one of the first and second side walls adjacent at least one of the first and second enhanced portions.

4. The absorbent structure of claim 1 in which the absorbent layer surface has a center line and the enhanced portions substantially abut one another along the absorbent layer center line.

5. The absorbent structure of claim 1 in which the transfer layer has a first longitudinal dimension and the absorbent layer has a second longitudinal dimension, the second longitudinal dimension being greater than the first longitudinal dimension.

6. The absorbent structure of claim 5 in which the transfer layer is substantially longitudinally centered under the absorbent layer to form absorbent layer extensions where the absorbent layer extends beyond the transfer layer.

7. The absorbent structure of claim 6 in which the absorbent layer contains superabsorbent particles.

8. The absorbent structure of claim 6 in which the absorbent layer extensions are compressed.

9. The absorbent structure of claim 1 in which the enhanced portion comprises at least three layers of the absorbent web.

10. An absorbent article comprising
    a body-facing, fluid-permeable layer and a garment-facing, liquid barrier layer,
    the fluid-permeable layer and the liquid-barrier layer substantially enclosing an absorbent structure,
    the absorbent structure having a longitudinal axis and comprising a substantially continuous absorbent web having first and second opposed side edges arranged substantially parallel to the longitudinal axis of the structure, the absorbent web comprising an absorbent layer in liquid communication with a transfer layer capable of transferring liquid to the absorbent layer, the transfer layer comprising a nonabsorbent material wherein:
    (1) the absorbent layer is superposed over the transfer layer to provide an outwardly facing absorbent layer surface and an opposed outwardly facing transfer layer surface;
    (2) the first edge of the absorbent web is arranged and configured wherein a region of the outwardly facing transfer layer surface proximate the first edge contacts a region of the outwardly facing absorbent layer surface to form a first enhanced portion;
    (3) the second edge of the absorbent web is arranged and configured wherein a region of the outwardly facing transfer layer surface proximate the second edge contacts a region of the outwardly facing absorbent layer surface to form a second enhanced portion; and
    (4) the first and second enhanced portions define a trough therebetween, and the trough is disposed toward the fluid-permeable layer.

11. The absorbent structure of claim 10 in which the transfer layer has at least one window provided therein at a predetermined location, thereby exposing the absorbent layer at the location.

12. The absorbent structure of claim 11 in which the structure has first and second ends substantially perpendicular to the longitudinal axis, the at least one window being located in at least one of the first and second enhanced portion adjacent at least one of the first and second ends.

13. The absorbent article of claim 10 in which the transfer layer has a first longitudinal dimension and the absorbent layer has a second longitudinal dimension which is greater than the first longitudinal dimension.

14. The absorbent article of claim 13 in which the transfer layer is substantially longitudinally centered under the absorbent layer to form absorbent layer extensions where the absorbent layer extends beyond the transfer layer.

15. The absorbent article of claim 14 in which the absorbent layer extensions are densified.

16. The absorbent article of claim 13 in which the absorbent layer has a center line and the enhanced portions substantially abut one another along the absorbent layer center line.

17. The absorbent article of claim 10 further comprising elastic means substantially parallel to the longitudinal axis.

18. An absorbent article comprising
  a body-facing, fluid-permeable layer and a garment-facing, liquid-barrier layer,
  the fluid-permeable layer and the liquid-barrier layer substantially enclosing an absorbent structure,
  the absorbent structure having a longitudinal axis and comprising first and second substantially continuous absorbent webs, the first absorbent web having first and second opposed side edges arranged substantially parallel to the longitudinal axis of the structure, the second absorbent web comprising third and fourth opposed side edges arranged substantially parallel to the longitudinal axis of the structure, the first absorbent web comprising a first absorbent layer in liquid communication with a first transfer layer capable of transferring liquid to the first absorbent layer, the first transfer layer comprising a nonabsorbent material, and the second absorbent web comprising a second absorbent layer in liquid communication with a second transfer layer capable of transferring liquid to the second absorbent layer, the second transfer layer comprising a nonabsorbent material wherein:
  (1) the first absorbent layer is superposed over the first transfer layer to provide a first, outwardly facing absorbent layer surface and an opposed first outwardly facing transfer layer surface of the first absorbent web, and the second absorbent layer is superposed over the second transfer layer to provide a second, outwardly facing absorbent layer surface and an opposed, second, outwardly facing transfer layer surface of the second absorbent web;
  (2) the first edge of the first absorbent web is arranged a configured wherein a region of the first, outwardly facing transfer layer surface proximate the first edge contacts a region of the first, outwardly facing absorbent layer surface to form a first enhanced portion;
  (3) the second edge of the first absorbent web is arranged and configured wherein a region of the first outwardly facing transfer layer surface proximate the second edge contacts a region of the first, outwardly facing absorbent layer surface to form a second enhanced portion;
  (4) the first and second enhanced portions of the first absorbent web define a first trough therebetween;
  (5) the third edge of the second absorbent web is arranged and configured wherein a region of the second, outwardly facing transfer layer surface proximate the third edge contacts a region of the second, outwardly facing absorbent layer surface to form a third enhanced portion;
  (6) the fourth edge of the second absorbent web is arranged and configured wherein a region of the second, outwardly facing transfer layer surface proximate the fourth edge contacts a region of the second, outwardly facing absorbent layer surface to form a fourth enhanced portion;
  (7) the third and fourth enhanced regions of the second absorbent web define a second trough therebetween; and
  (8) the second absorbent web is disposed within the trough of the first absorbent web; and
  the fluid-permeable layer is disposed toward the first and second troughs.

19. The absorbent structure of claim 1 wherein the transfer layer substantially surrounds the absorbent layer at the first and second enhanced portions.

20. The absorbent article of claim 10 wherein the transfer layer substantially surrounds the absorbent layer at the first and second enhanced portions.

* * * * *